United States Patent [19]

Van Es

[11] Patent Number: 5,501,341
[45] Date of Patent: Mar. 26, 1996

[54] CATHETER PACKAGING

[75] Inventor: Bert Van Es, Roden, Netherlands

[73] Assignee: Cordis Corporation, Miami Lakes, Fla.

[21] Appl. No.: 384,844

[22] Filed: Feb. 7, 1995

[30] Foreign Application Priority Data

Feb. 10, 1994 [NL] Netherlands ............................ 9400214

[51] Int. Cl.⁶ .................................................. B65D 85/20
[52] U.S. Cl. ........................................... 206/364; 206/476
[58] Field of Search ..................................... 206/363, 364,
206/365, 476–478, 482, 483, 486–489

[56] References Cited

U.S. PATENT DOCUMENTS

| | | | |
|---|---|---|---|
| 435,094 | 8/1890 | Hewitt | 206/476 |
| 2,224,027 | 12/1940 | Tate | 206/476 |
| 2,947,415 | 8/1963 | Garth | 206/364 |
| 3,967,728 | 7/1976 | Gordon et al. | 206/364 |
| 4,023,678 | 5/1977 | Fiedler | 206/363 |
| 5,131,537 | 7/1992 | Gonzales | 206/364 |
| 5,351,822 | 10/1994 | Sinn | 206/363 |

*Primary Examiner*—Jimmy G. Foster
*Attorney, Agent, or Firm*—Thomas R. Vigil

[57] ABSTRACT

The packaging for a catheter comprises a card received in an envelope, which is provided with a row of retaining elements with lips formed by cuts, each of which can be bent out of the surface of the card around a bending line defined by the ends of the cut concerned. Each retaining element comprises at least one push down lip, which can extend across the catheter and an opposing enclosing lip, and a lateral edge of the enclosing lip directed towards the push down lip extends mainly parallel to the row.

4 Claims, 2 Drawing Sheets

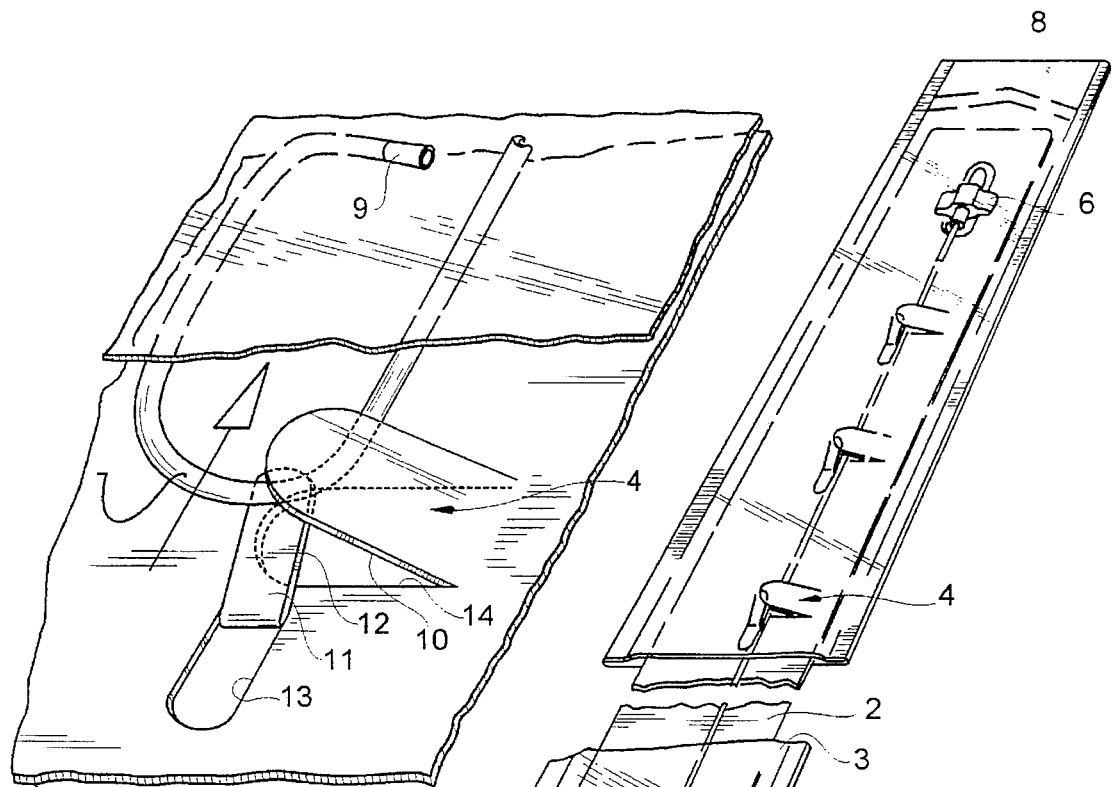
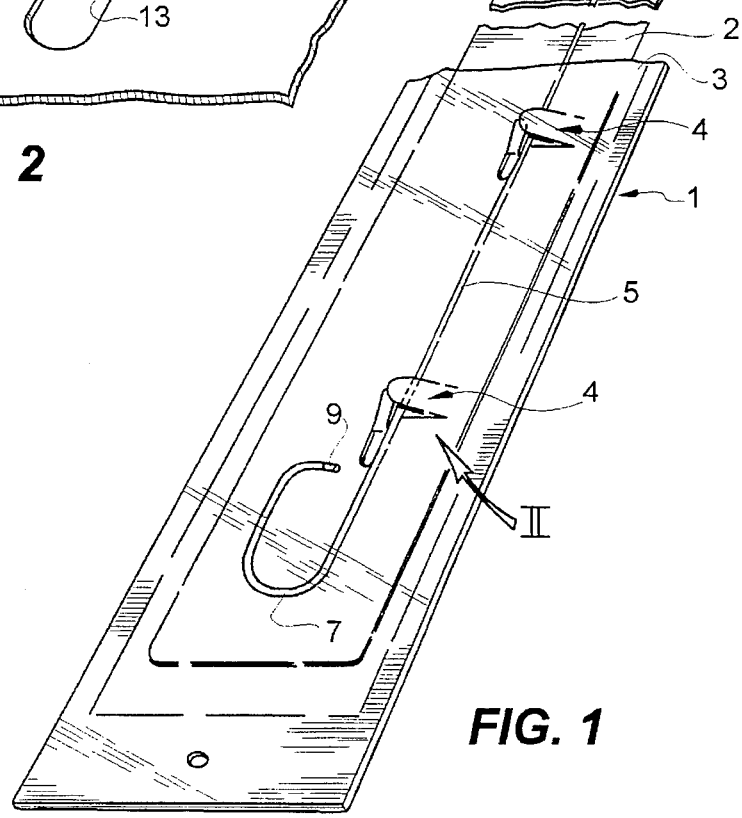
FIG. 2
FIG. 1

CATHETER PACKAGING

BACKGROUND OF THE INVENTION

1. Field of the Invention

The present invention relates to packaging for a catheter comprising a card received in an envelope. This card is provided with a row of retaining elements with lips formed by cuts, each of which can be pushed out of the surface of the card. The catheter is secured under these lips and inserted like this, together with the card, into the envelope, or the envelope is formed in one mechanical packaging process around the card, after which the envelope is sealed hermetically and the entire package is sterilized for future use.

2. Description of the Prior Art

In prior catheter packages, when using the catheter, it will be taken out of the package by opening an envelope at one end, taking hold of the catheter and pulling it along its length from the envelope. When doing so, the catheter will be pulled along and through the retaining elements.

The envelope is opened, for instance, on the side where the connecting member of the catheter is situated. When pulling the catheter from the envelope, the end of the catheter which is to be introduced into the patient will pass through all the retaining elements.

This end usually has a specific curved shape which tends to get stuck in the retaining elements. As the material of which the catheter has been made, and, more particularly, of which the distal end-section is made, is soft in order to prevent trauma to a patient, damage can be caused to the catheter by the relatively sharp and hard edges of the lips when pulling it out, which can even result in uselessness of the catheter.

Several examples of prior art packages are disclosed in the following U.S. Patents:

| U.S. Pat. No. | Patentee |
| --- | --- |
| 3,967,728 | Gordon |
| 5,131,537 | Gonzales |

SUMMARY OF THE INVENTION

The object of the invention is to provide catheter packaging of the type described above from which a catheter can be removed without running the risk of damage to the catheter.

This aim is achieved with catheter packaging comprising: a card received in an envelope, which is provided with a row of retaining elements with lips formed by cuts which can be bent out of the surface of the card around a bending line defined by the ends of the cut, each retaining element comprising at least one push down lip, which can extend across the catheter and an opposing enclosing lip, a lateral edge of the enclosing lip that is directed towards the push down lip extending mainly parallel to the row.

On the passing of the catheter and, in particular, on the passing of its curved end-section, the enclosing lip can easily bend towards the surface of the card without being impeded by the catheter. Thus, a free passage is created through which the catheter can pass without running the risk of damage.

The catheter is placed in such a way on the packaging that the bending line of the enclosing lips is always turned towards the most delicate, as a rule the distal end of the catheter.

The bending line defined by the ends of the cut forming the enclosing lip preferably is at right angles to the row.

In this way, the enclosing lip offers a minimum of resistance when bending away in the longitudinal direction of the row but a maximum of resistance in the traverse direction in order to carry out the retaining function optimally.

The cut defining the enclosing lip can be situated on that side of its bending line which is turned away from the accompanying push down lip and can have a length at right angles to this bending line which is longer than the distance of that bending line to the push down lip, so that the enclosing lip can be bent back to a position underneath the push down lip.

By bending the enclosing lip backwards under the push down lip, the enclosing lip is forced upwards by the inherent elastic properties of the material of which the card is made, making contact with the push down lip, so that the push down lip and the enclosing lip of each retaining element form a properly closed unit. Forces exerted during transport, etc. on the enclosing lip are only directed towards the bending line, so that the enclosing lip does not yield when such forces occur. Consequently, the catheter remains properly fastened in its packaging in transit. When taking the catheter from the packaging, the enclosing lip can yield easily due to the forces acting at that moment in a transverse direction on the bending line, as a result of which the catheter can pass the enclosing lip without appreciable hindrance and chance of damage.

The push down lip can be a U-shaped lip with a bending line parallel to the row and the enclosing lip a U-shaped lip with a bending line at right angles to the row.

BRIEF DESCRIPTION OF THE DRAWINGS

The invention is explained below in the following description with reference to the embodiments illustrated in the accompanying drawings wherein:

FIG. 1 shows a partly broken away view of packaging, constructed according to the teachings of the present invention, containing a catheter.

FIG. 2 represents a detailed view at arrow II in FIG. 1.

DESCRIPTION OF THE PREFERRED EMBODIMENT(S)

Figure 3:
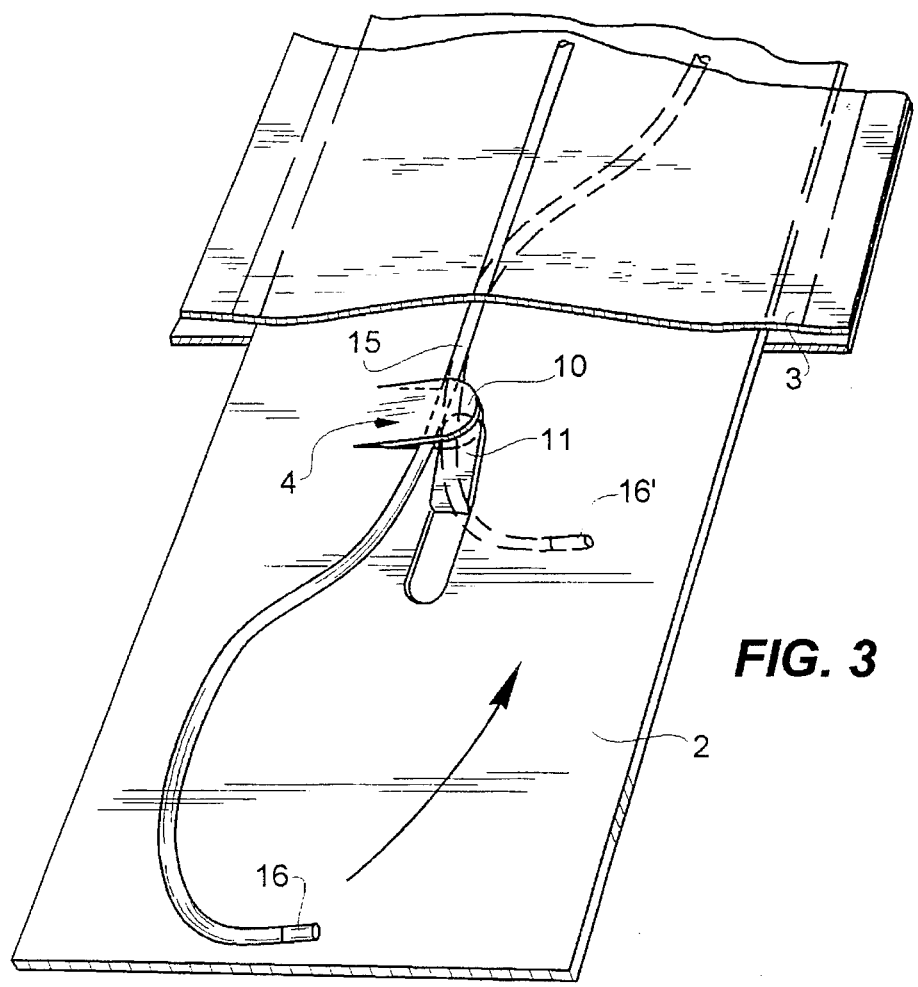
FIG. 3 shows a view of the packaging according to the invention corresponding to FIG. 2 but with a differently shaped catheter.

The packaging 1, according to the invention shown in FIG. 1, comprises a card 2 which is provided with a row of retaining elements. A catheter 5 is held in a secure position on the card 2 by retaining elements 4, which will be explained in greater detail hereinafter.

The card 2 with the catheter 5 on it is received in an envelope 3 which is subsequently sealed hermetically and sterilized.

When using the catheter 5, the envelope 3 will be opened under sterile conditions at the end 8. In order to remove the catheter 5, the attending physician will take hold of its connecting element 6 and pull the catheter 5 in a longitudinal direction from the packaging. In doing so, the catheter 5 will be pulled out of the retaining elements 4. Especially the passing of the distal end 7 of the catheter 5 is critical.

As shown more clearly in FIG. 2, each retaining element 4 comprises a push down lip 10 and an enclosing lip 11. Both lips 10 and 11 are formed by cuts 14, 13, respectively, in the material of the card 2. As best shown in FIGS. 1 and 2, the push down lip 10 retains the catheter 5 in the right hand direction while the enclosing lip 11 wedges the catheter 5 to prevent movement only in the left hand direction. The lateral edge 12 of the enclosing lip 11 directed towards the push down lip 10 extends, as is shown most clearly in FIGS. 1 and 2, parallel to the row of retaining elements 4. Because of this, the lip 11 can bend unimpeded towards the surface of the card 2, also when a catheter 5 has been received in the retaining element 4.

When pulling the catheter 5 out, the bent section of the distal end 7 of the catheter 5 easily forces the enclosing lip 11 down, so that the catheter 5 does not grate along the sharp edges of the lips 10 or 11 or jams between the card 2 and the lips. Thus, the distal end 7 can be pulled out very easily past all the retaining elements 4 without any risk of damage. The tip 9 of the distal end 7 is indicated as a separate element, which usually is made of a soft material which does not cause trauma, does not even make any contact at all with the retaining elements 4.

As FIGS. 1 and 2 illustrate, the bending line of the enclosing lip 11, which is defined by the ends of the cut 13, is at right angles to the longitudinal direction of the row of retaining elements 4. This contributes to a performance of lip 11 which can be used for the intended purpose. The push down lip 10 has a bending line which extends parallel to the row of retaining elements 4.

With the embodiment shown, the cut 13 of the enclosing lip 11 is situated on that side of its bending line which is turned away from the push down lip 10. This cut 13 and therefore the lip 11 is longer than the distance from the bending line of that lip 11 to the push down lip 10. For this reason, the enclosing lip 11 can be bent back to underneath the push down lip 10 as shown. Because of the springy nature of the material of which the card 2 has been made, usually thick paper or thin cardboard, the lip 11 is subjected to a bias acting in an upward direction which keeps it properly up and in contact with the push down lip 10. Thus, it is ensured that the catheter 5 is secured properly in every retaining element under all circumstances, until the catheter 5 is removed from the packaging for use.

The position of the retaining elements 4 on the card 2 depends on the catheter 5 to be packed. With the embodiment of FIG. 1, they have, for instance, been arranged at one side with the enclosing lips 11 pointing inwards.

With a catheter 5 with a differently shaped distal end, for instance, the catheter 15 as shown in FIG. 3, the retaining elements 4 have been arranged more towards the center. In FIG. 3, the elements which correspond to those shown in FIGS. 1 and 2, have been indicated with the same reference numbers.

In actual practice, two embodiments of the card 2 suffice. In both embodiments, the retaining elements 4 are arranged at the same distance from the edge of the card 2, but with one embodiment the enclosing lips 11 point outwards and with the other embodiment they point inwards. The card 2 to be used for a specific catheter 15 is chosen in such a way that when pulling the catheter 15 from the packaging, the end section will always slide over the enclosing lip 11 to prevent damage.

In FIG. 3, the retaining element 4 has been arranged more or less in the center of the card 2, whereby the enclosing lip 11 has been moved sideways on the card 2. The enclosing lip 11 is situated, however, just as is the case with the embodiments of FIGS. 1 and 2, on that side of the retaining element 4 to which the tip 16 of the catheter is pointing. On removing the catheter 15, the enclosing lip 11 is consequently also pressed down by the curved section of the catheter 15, and enables this curved section to pass without the tip 16 making contact with the lips 10, 11 of the retaining element. In FIG. 3, the position of the curved end of the catheter 15 when passing the retaining element 4 has been indicated with dotted lines.

Figure 4:
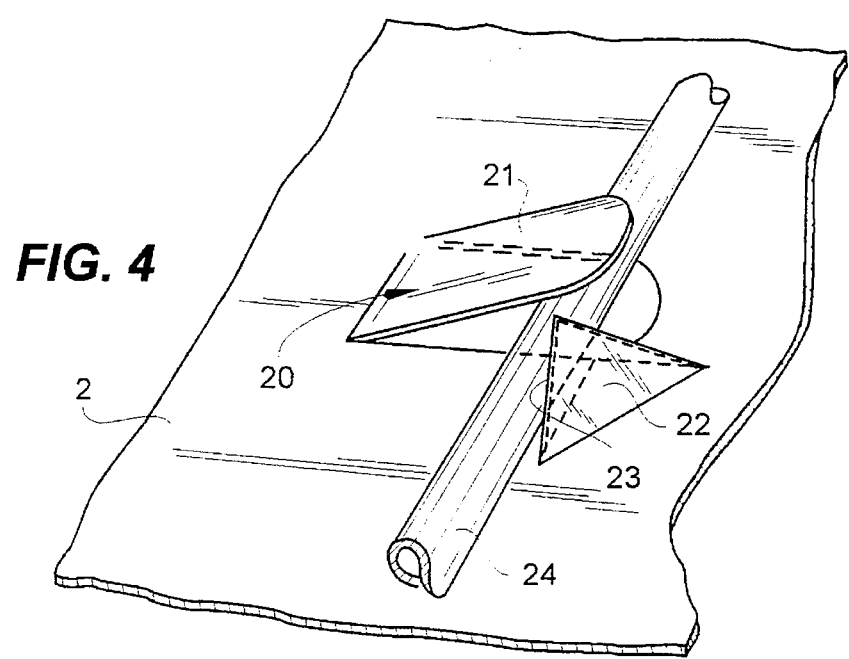
FIG. 4 illustrates another alternative embodiment of a retaining element for packaging constructed according to the teachings of the present invention.

FIG. 4 illustrates part of the packaging according to the invention at the retaining element 20. The retaining element 20 also comprises a push down lip 21 and an enclosing lip 22. The push down lip 21 secures the catheter 24 on the card in a downward, and as seen in FIG. 4 left-hand direction. The enclosing lip 22 secures the catheter 24 in the right-hand direction.

The lateral edge 23 of the enclosing lip 22 turned towards the push down lip 21 extends, as illustrated in FIG. 4, parallel to the catheter 24 and consequently parallel to the row of retaining elements 20. When removing the catheter 24 from the packaging the enclosing lip 22 can be pressed down easily as a result of which the catheter 24, and in particular its curved end-section, can pass without any problems.

In a manner corresponding to the previous Figures, a catheter will be received in packaging with retaining elements 20 in such a way, that the sensitive tip of the catheter 24 is pointing in the same direction as the enclosing lip. When removing the catheter 24, the curved section of the catheter 24 will push the enclosing lip 22 down and the tip will be able to pass without making contact with the retaining element 20.

The invention is not to be limited to the embodiments illustrated in the Figures. Also, the shape of the lips of the retaining elements can vary considerably.

I claim:

1. Packaging for a catheter comprising: a card received in an envelope, which is provided with a row of retaining elements with lips formed by cuts which can be bent out of the surface of the card around a bending line defined by the ends of the cut, each retaining element comprising at least one push down lip, which can extend across the catheter and an opposing enclosing lip, a lateral edge of the enclosing lip that is directed towards the push down lip extending mainly parallel to the row.

2. Packaging as claimed in claim 1 wherein the bending line defined by the ends of the cut forming the enclosing lip is at right angles to the row.

3. Packaging as claimed in claim 1 wherein the cut defining the enclosing lip is situated on that side of its bending line which is turned away from the accompanying push down lip and has a length at right angles to this bending line which is longer than the distance of that bending line to the push down lip, so that the enclosing lip can be bent back to a position underneath the push down lip.

4. Packaging as claimed in claim 3 wherein the push down lip is a U-shaped lip with a bending line parallel to the row and the enclosing lip a U-shaped lip with a bending line at right angles to the row.

* * * * *